United States Patent
Ehnholm et al.

(10) Patent No.: US 6,671,538 B1
(45) Date of Patent: Dec. 30, 2003

(54) INTERFACE SYSTEM FOR USE WITH IMAGING DEVICES TO FACILITATE VISUALIZATION OF IMAGE-GUIDED INTERVENTIONAL PROCEDURE PLANNING

(75) Inventors: Gösta Jakob Ehnholm, Helsinki (FI); Teuvo Vaara, Veikkola (FI); Erkki Vahala, Helsinki (FI)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/449,813

(22) Filed: Nov. 26, 1999

(51) Int. Cl.$^7$ .................................................. A61B 5/00
(52) U.S. Cl. ........................................ 600/425; 382/131
(58) Field of Search ................................ 382/128, 131; 600/425, 427, 429, 410, 417, 173, 407; 606/130

(56) References Cited

U.S. PATENT DOCUMENTS

| | | | |
|---|---|---|---|
| 5,515,160 A | | 5/1996 | Schulz et al. ................ 356/241 |
| 5,638,819 A | | 6/1997 | Manwaring et al. ..... 128/653.1 |
| 5,682,890 A | * | 11/1997 | Kormos et al. .......... 128/653.2 |
| 5,740,267 A | * | 4/1998 | Echerer et al. ............. 382/132 |
| 5,799,055 A | * | 8/1998 | Peshkin et al. ............... 378/42 |
| 5,921,992 A | * | 7/1999 | Costales et al. ............ 606/130 |
| 5,987,349 A | * | 11/1999 | Schulz ........................ 600/427 |
| 6,006,126 A | * | 12/1999 | Cosman ...................... 600/426 |
| 6,036,637 A | * | 3/2000 | Kudo ........................... 600/173 |
| 6,069,656 A | * | 5/2000 | Silver ........................... 348/169 |
| 6,119,032 A | * | 9/2000 | Martin et al. ................ 600/411 |
| 6,167,296 A | * | 12/2000 | Shahidi ....................... 600/427 |

FOREIGN PATENT DOCUMENTS

| | | |
|---|---|---|
| EP | 0469966 A1 | 2/1992 |
| EP | 0922438 A1 | 6/1999 |
| WO | WO 9731581 A | 9/1997 |

* cited by examiner

*Primary Examiner*—Marvin M. Lateef
*Assistant Examiner*—Eleni Mantis Merlader
(74) *Attorney, Agent, or Firm*—Fay, Sharpe, Fagan, Minnich & McKee, LLP (57) ABSTRACT

An interface system is provided for planning a surgical procedure for inserting an object into a patient along a surgical planning trajectory from an entry point on the patient to a target point within the patient. Using an imaging device, a first scan of the patient is performed to generate a first image volume data set of a first area of the patient. A first sectional image of the patient is displayed on a human-readable display device associated with the imaging device. The first sectional image is based on the first image volume data set. Using an operator interface device, a second planning image of the patient is defined by placing a plurality of graphical point symbols in the first sectional image of the patient displayed on the display device. The plurality of graphical point symbols define a second area of the patient to be subject of display as a second sectional image of the patient. The second sectional image of the patient is derived either directly from the first image volume data set, indirectly from the first image volume data set by interpolation, or by performing a second scan of the patient with the imaging device.

32 Claims, 6 Drawing Sheets

INTERFACE SYSTEM FOR USE WITH IMAGING DEVICES TO FACILITATE VISUALIZATION OF IMAGE-GUIDED INTERVENTIONAL PROCEDURE PLANNING

BACKGROUND OF THE INVENTION

The present invention relates to the art of interactive image-guided surgery. It finds particular application in conjunction with the planning stage of minimally invasive surgery performed in magnetic resonance imaging systems using free-hand guide devices to orient surgical tools such as biopsy probes or the like and will be described with particular reference thereto. It is to be appreciated, however, that the invention is also applicable to a wide range of imaging equipment and minimally invasive surgical procedures including those performed using CT scanners, ultrasonic, fluoroscopic, and other imaging devices and surgeries using those devices.

Heretofore, several systems have been proposed combining mechanical arm type mechanisms or free hand localizers together with human anatomy imaging devices for performing certain interventional surgical procedures such as, for example, the placement of catheters, drainage tubes, biopsy probes, or the like, within a patient's body. In one such system described in U.S. patent application Ser. No. 08/980, 337, filed Nov. 28, 1997 and assigned to the assignee of the instant application, a multi-jointed mechanical arm assembly is mounted in a fixed relationship to a CT scanner device. The mechanical arm assembly carries a surgical planning device for defining a physical trajectory extending from the mechanical arm assembly and through the body of a patient disposed on the CT scanner. In addition, the CT scanner includes a virtual needle display for planning the introduction of an object such as a biopsy probe into the patient from an entry point along a virtual trajectory shown on the display towards a virtual target point within the patient. The display includes a plurality of spaced transverse axial views taken through the patient including an image slice corresponding to the virtual needle entry point on the patient as well as a second transverse axial view of the patient taken on an image slice of the image volume data set corresponding to the target point within the patient. Other views of the patient that are co-planar with the virtual needle trajectory are useful for planning minimally invasive surgical procedures to avoid critical anatomical structures such as, for example, sensitive nerves, blood vessels or arteries, critical organs and the like. The system described also includes a manual virtual needle "depth" control and provides a corresponding display of same to further assist interventionists during the planning stage.

Although the above system and others have met with success and provide adequate results, the displays of the virtual tool path trajectory are not updated in real time to follow localizer motion. More particularly, in order to provide the most complete and accurate virtual representation of the patient's anatomy and virtual tool trajectory extending therethrough, the system performs a series of interpolation steps to develop the multiple image planes co-planar with the virtual needle trajectory for display based on an initially acquired image volume data set.

Of course, numeric interpolation requires time. This being the case, the displays presented to an interventionist often "lag" quick gross motions of the mechanical arm assembly, and/or the surgical planning tool carried thereon. Another drawback of numerical interpolation, particularly when only a limited number of image slices are available, is that the overall image is degraded and the image appearance typically changes. This makes interpretation of the image more difficult and visualization of the procedure or planning less direct.

It is therefore desirable to provide a system for generating an essentially "real time" set of displays showing a virtual needle trajectory extending through virtual anatomy for planning image-guide interventional procedures. Preferably, there is little or no noticeable lag time between quick motions of the localizer planning device and the one or more virtual displays thereof.

In addition, it would be desirable to provide a system that generates a second display of an area of a first display selected by an interventionist by placing a plurality of graphical point symbols in the first display. Preferably, the second display is derived directly from a first image volume data set collected from the patient so that further re-scanning of the patient is unnecessary. Alternatively, the second display is based on an interpolation of the first image volume data set. Still alternatively, the second display is derived from a second image volume data set collected from the patient during a second scan of the patient. Preferably, the area of the patient scanned during the re-scan is bounded by the plurality of graphical point symbols.

Still in addition, it would be desirable to provide a system that generates a vertical bulls-eye target to enable visualization of the correctness of motion of a localizer device relative to a patient in size and/or color as the surgical tool carried on the localizer device first becomes aligned with the trajectory and then as the device reaches the target point.

The present invention provides a new and improved interface system for use with imaging devices to facilitate real time visualization of image-guided interventional procedure planning which overcomes the above-reference problems and others.

SUMMARY OF THE INVENTION

In accordance with the present invention, a method of planning a surgical procedure for inserting an object into a patient along a surgical planning trajectory from an entry point on the patient to a target point within the patient is provided. Using an imaging device, a patient is scanned to generate a first image volume data set of a first area of the patient. The image volume data set is formed of a plurality, preferably five (5) parallel two-dimensional image slices of the patient spaced apart along an axial axis aligned substantially with the head-to-toe axis of the patient. Using a human-readable display device associated with the imaging device, the first sectional image of the patient based on the first image volume data set is displayed. A second scan of the patient using the imaging device is planned with an operator interface device associated with the imaging device. A plurality of graphical point symbols are placed in the first sectional image of the patient displayed on the display device. The plurality of graphical point symbols define a second area of the patient to be subject of the second scan to generate a second image volume data set.

Further in accordance with the present invention, a second scan of the patient is performed using the imaging device to generate the second image volume data set of the patient. The second image volume data set is derived from the second area of the patient and is substantially bounded by the plurality of graphical point symbols placed in the second scan planning step.

In accordance with a more limited aspect of the invention, indicia are displayed on the display device of a position of each of the plurality of graphical point symbols relative to a plane through the first image volume data set defining the first sectional image. The indicia include first indicia indicating first ones of the graphical point symbols that are located between the plane on the display device and a human observer of the display device. Second indicia indicate second ones of the graphical point symbols that are located behind the plane of the display device relative to the human observer of the display device. Third indicia are displayed indicating a relative distance between the graphical point symbols and the plane.

In accordance with yet a further aspect of the invention, the step of planning the second scan of the patient by placing the plurality of graphical point symbols includes placing a first graphical point symbol in the first sectional image representative of a target point for an interventional surgical procedure on the patient. Further, the step of planning the second scan of the patient includes placing a second graphical point symbol in the first sectional image representative of an entry point before the interventional procedure on the patient.

In accordance with a still further aspect of the invention, the second scan of the patient is planned to generate a second sectional image of the patient orthogonal to a line connecting the entry point to the target point. Alternatively, the second scan of the patient is planned to generate the second sectional image of the patient parallel to the line connecting the entry point to target point.

In accordance with a second embodiment of the invention, an interface system is provided for use with an associated imaging device. The interface system is selectively operative to execute a scan of a patient to generate a first image volume data set of the patient. The interface system includes a human-readable display device associated with the imaging device for selectively displaying a plurality of first image slices of the patient taken from the first image volume data set. In addition, an operator interface device is provided in association with the imaging device. The operator interface device is operative to define spatial properties of a second set of image slices to be taken from the first image volume data set. The spatial properties of the second set of image slices to be taken from the first image volume data set are defined by selectively placing a plurality of graphical point symbols in the plurality of first image slices of the patient displayed on the display device.

In accordance with a further aspect of the second embodiment of the invention, the interface system includes interpolating means for generating the second set of image slices by interpolating the first image volume data set. In addition, means are provided for generating the second set of image slices as a maximum intensity projection image of the first image volume data set. The maximum intensity projection image represents a three-dimensional rendering of selected tissue within the patient.

It is a primary advantage of the present invention that visualization information is provided on a human-readable display monitor in substantially real time to track the motion of a localization device relative to a patient's body.

It is another advantage of the present invention that a set of graphical symbols are provided for display on the human-readable display monitors. The graphical symbols include indicia regarding the relative position of the virtual planning trajectory relative to the one or more image planes shown on the display device. Other graphical symbols include a symbol representative of a virtual localizer device, a target point within the patient's body, an entry point showing a point of intersection between the patient's body and the planning trajectory, and a pivot point for fully determining the image plane. When expedient, the pivot point is chosen to include some selected regions of interest in the imaging plane such as, for example, a blood vessel or other tissue to be avoided during the surgical procedure.

Still other advantages and benefits of the invention will become apparent to those skilled in the art upon a reading and understanding the following detailed description.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein.

DETAILED DESCRIPTION OF THE PREFERRED EMBODIMENTS

Figure 1:
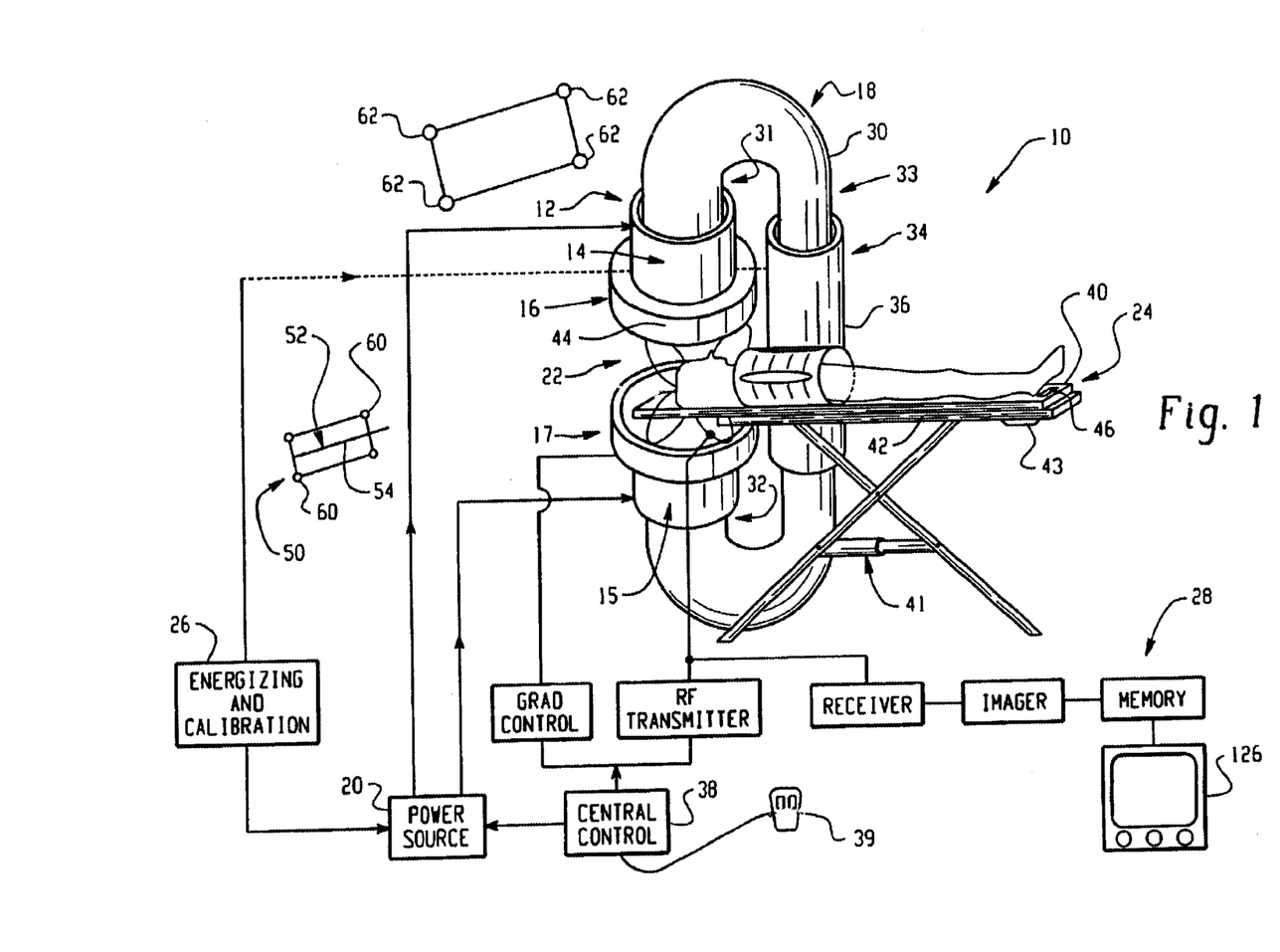
FIG. 1 is a diagrammatic illustration of a "C magnet" type magnetic resonance imaging device using an interface system in accordance with the present invention.

Referring now to the drawings wherein the showings are for the purposes of illustrating the preferred embodiments of the invention only and not for purposes of limiting same, with reference first to FIG. 1, the subject invention is shown in use with an open "C" magnetic resonance (MR) imaging device 10 of the type well known in the art. Since the imaging device 10 forms no part of the present invention, it will be described with a minimum of detail. As shown in the FIGURE, the "C" type MR imaging device 10 includes a magneto motive force means 12 in the form of a pair of resistive magnet drivers 14, 15 disposed adjacent pole pieces 16, 17 on opposite ends of a C-shaped ferromagnetic flux path 18. The magneto motive force means 12 together with a magnetic flux stabilizing means 20 creates and stabilizes a magnetic field across an air gap 22 between the pole faces and along the ferromagnetic flux path 18. A retractable patient support 24 selectively supports a patient or subject to be examined in the air gap 22 defined between the pole faces. An energizing and calibration system 26 is used to set up the magnetic field across the air gap 22. Magnetic resonance electronics 28 selectively induce magnetic resonance of dipoles in the image region and process resultant received magnetic resonance signals to create an image or other diagnostic information.

The ferromagnetic flux path 18 includes a C-shaped ferromagnetic member 30 having a first end 31, a second end 32, and a middle portion 33. The first pole piece 16 on the first end 31 of the flux path together with the second pole piece 17 on the second end 32 define the air gap 22 therebetween. The C-shaped member 30 is configured to minimize the length of the ferromagnetic flux path while spacing the ferromagnetic flux path sufficiently from the gap to minimize distortion to the magnetic field in the air gap.

The magnetic flux stabilizing means 20 includes a superconducting cryodriver 34 which encircles a segment of the middle portion 33 of the C-shaped ferromagnetic member 30. As is well known by those skilled in the art, the cryodriver 34 includes a cryostat 36 which houses an annular superconductor magnet that encircles the flux path. Alternatively, the magnetic flux can be generated by coils made of aluminum or copper conductors, for example, and energized by a precision current supply.

The patient support 24 includes a patient supporting surface 40 in a substantially horizontal plane. The supporting surface has a longitudinal axis lengthwise therealong and a perpendicular transverse axis there across, both in the horizontal plane. An elevation adjusting means 41 selectively adjusts the relative height of the supporting surface. The supporting surface is slidably mounted on a support frame 42 to provide a means for moving the supporting surface in the horizontal plane. Preferably, a motor drive 43 is mounted to the frame to drive the patient supporting surface therealong.

A surgical instrument guidance and localizer device 50 is adapted to selectively carry a minimally invasive surgical instrument 52. The localizer device 50 is positionable relative to the patient by an interventionist during pre-surgical planning and while carrying out surgical procedures in accordance with the present invention. The surgical instrument in the illustrated embodiment includes a manually guided biopsy needle 54 adapted to engage the guidance device 50 and slide therealong to enter the patient's body along a precise trajectory and extract a piece of tissue from a precise location for analysis. It is to be appreciated, however, that numerous other instruments and guidance devices are contemplated.

It is to be noted that the position and orientation of the localizer device 50 and the minimally invasive surgical instrument 52 mechanism carried thereon are monitoring by the imaging device 10. Preferably, passive optical tracking, such as available from Northern Digital Inc. under their tradename POLARIS™ is used. Passive optical tracking of the localizer device 50 removes the need for cable connections and/or power supplies at the localizer device. Alternatively, active or hybrid optical or other tracking systems can be used as well.

A plurality of passive reflective targets, such as retroreflective spheres or disks 60 are mounted on the localizer device 50 in a fixed, known relationship to the minimally invasive surgical tool 52. A corresponding array of transmitters and receivers 62 is mounted in a fixed relationship to the imaging apparatus 10, preferably affixed to the ceiling of the room. Each time the transmitters are actuated and the emitted signal is reflected from the passive reflective targets 60 and then received by the receivers 62, the position and orientation of the localization device 50 and therefore of the surgical instrument 52 carried thereon are accurately and quickly calculated substantially in real time using geometric triangulation techniques. By positioning the localization device on a plurality of markers 44 disposed in a known, fixed relationship to the coordinate system of the imaging apparatus 10, the coordinate systems of the surgical instrument 52 and the imaging apparatus 10 can be readily correlated. Analogously, by positioning the localization device 50 on a calibration and verification area 46 formed on the patient table 24, the coordinate system of the surgical instrument 52 and the patient table 24 can be readily coordinated.

To verify the orientation and position of the guidance device 50 relative to the patient support, a tip of the guidance device or a pointer carried thereon is touched to the calibration and verification area 46 and an assessment is made whether the electronic signals indicative of patient support location and surgical instrument location, in fact, place both at the same point in space. Similarly, one or more markers 44 on the imaging apparatus in a fixed, known location relative to a plane of the magnetic resonance signals is touched by the tip of the guidance device or pointer and the electronic position signals are compared to be sure that the coordinate systems of the volumetric scanner 10 and the guidance device 50 are accurately correlated.

Figure 2:
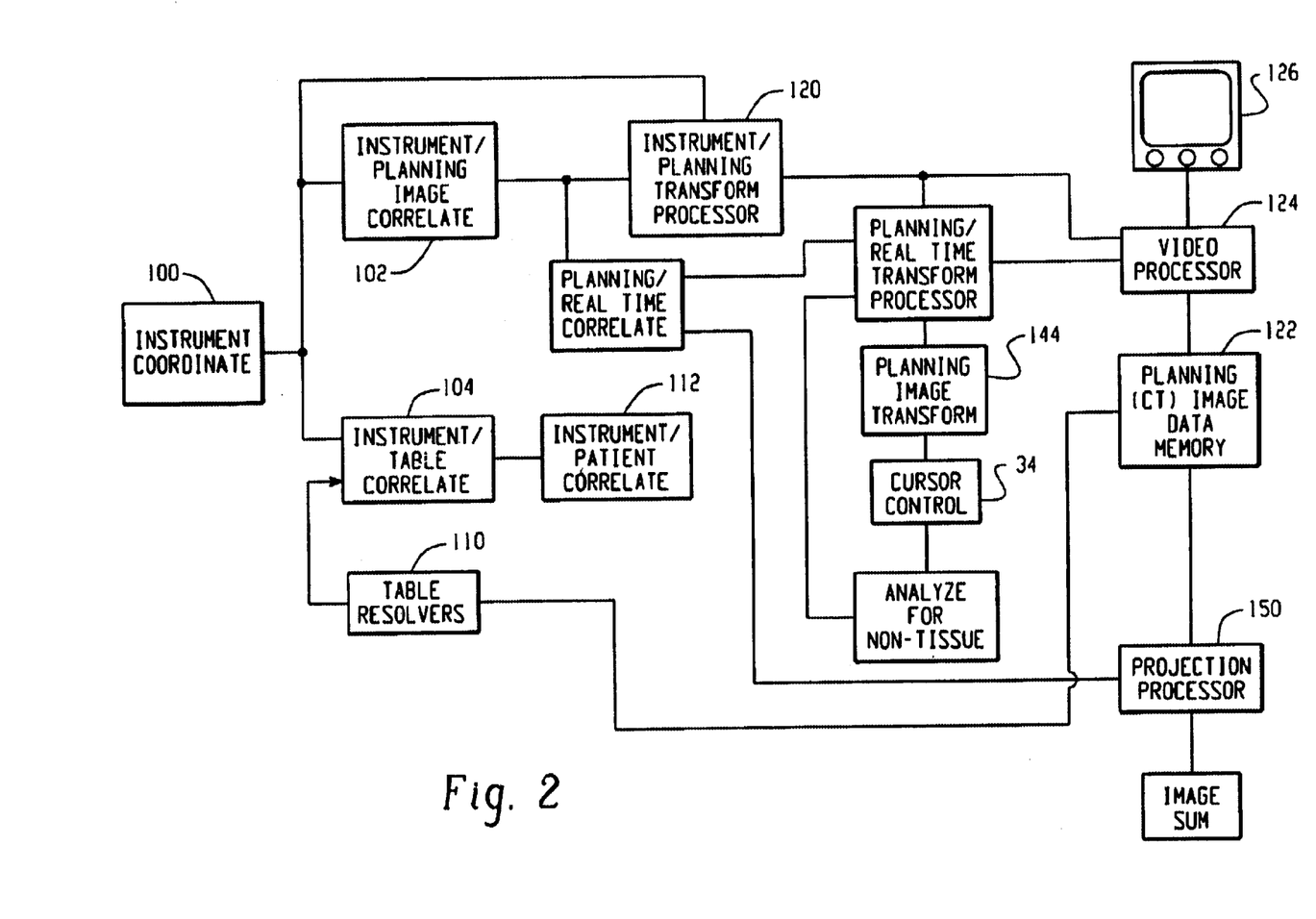
FIG. 2 is a diagrammatic illustration of the image acquisition and planning image processing performed by the systems of the invention.

With reference to FIG. 2, an instrument coordinate circuit 100 determines the position and trajectory of the surgical instrument 52 carried on the guidance device 50 in instrument space, particularly a coordinate system of the instrument. The instrument coordinate circuit is connected with the receivers 62 to receive signals indicative of changes of position and orientation of the instrument in instrument space. An instrument-planning scanner correlating processor 102 determines the correlation or transform between the minimally invasive surgical instrument 52 and the volumetric scanner 10 coordinate systems. The correlation or transform is normally described in terms of offset (particularly offset along the axis of the patient support), angular offset or rotation, and scaling. In one embodiment, the instrument 52 is touched to three or more markers 44 which are in a known relationship to the volumetric scanner coordinate system.

By measuring the coordinates of the instrument in the instrument coordinate system while touching each marker, three or more common points in the two coordinate systems are determined. By determining a barrycenter, centroid, or other characteristic point of the common points, the offset between the two coordinate systems is determined. By determining the angular difference between the rays from the characteristic point to each point in each coordinate system, the angular offset is determined. By determining a difference in physical displacement between the characteristic point and the corresponding points in each coordinate system, the scaling factor is determined. Of course, in a system such as the illustrated embodiment in which the instrument and the volumetric scanner are electronically linked by arrays of emitters and receivers, the transform or relationship between the volumetric scanner and the instrument coordinate systems are determined during a calibration of the electronic system during installation. The touching of the markers can be eliminated or used merely to confirm that the instrument and the MR scanner coordinates have not become misaligned.

An instrument-to-patient table correlating processor 104 performs a similar calculation or uses similar known physical relationships to determine the correlation or transform between the patient table and the surgical instrument. Preferably, a phantom having a multiplicity of marks is disposed in a known position on the table to provide a larger number of corresponding points in both coordinate systems for the correlating process. Images of the phantom can be used to derive transforms between the patient table space and planning or real time image coordinate systems.

Table resolvers 110 located in the patient table 24 contribute vertical and longitudinal offsets to the correlation between the instrument and the patient table when the table is raised or lowered and when the patient supporting surface 40 is moved axially. An instrument-to-patient correlation processor 112 determines the correlation between the instrument coordinate system and a patient coordinate system.

Again, this is preferably done by placing the instrument on three or more known reference points on the patient. Such points may include readily identifiable anatomical structures such as the tip of the nose, distinctive points on bones, fiducial markers that are imaged during the volumetric imaging process, or the like.

An instrument-to-volumetric image coordinate system transform processor 120 receives the correlation or transform from the instrument-to-planning scanner correlating processor 102. The instrument-to-volumetric image processor operates on input position and orientation coordinates in image space to transform them into volumetric image data space or vice-versa. Knowing the position of the surgical instrument in volumetric or planning data space enables the position of the instrument and orientation of same to be superimposed on the volumetric planning image data.

During a medical procedure, the patient is positioned in the imaging apparatus and a volumetric image data set is generated. The volumetric image data set is stored in a volumetric or planning data memory 122. The position of the patient during the generation of the planning data, particularly as the table moves to generate spiral or slice data, is stored in conjunction with the volumetric planning data such that the data is correlated with the patient table coordinate system. The operator control 38 controls the volume planning image data memory or a video processor 124 such that selected slices, projection images, surface renderings, or other conventional displays of the data are generated for display on a planning image display 126. Preferably, the planning image display includes corresponding sagittal, coronal, and transverse axial slices through one or more selected common points of intersection.

Figure 3:
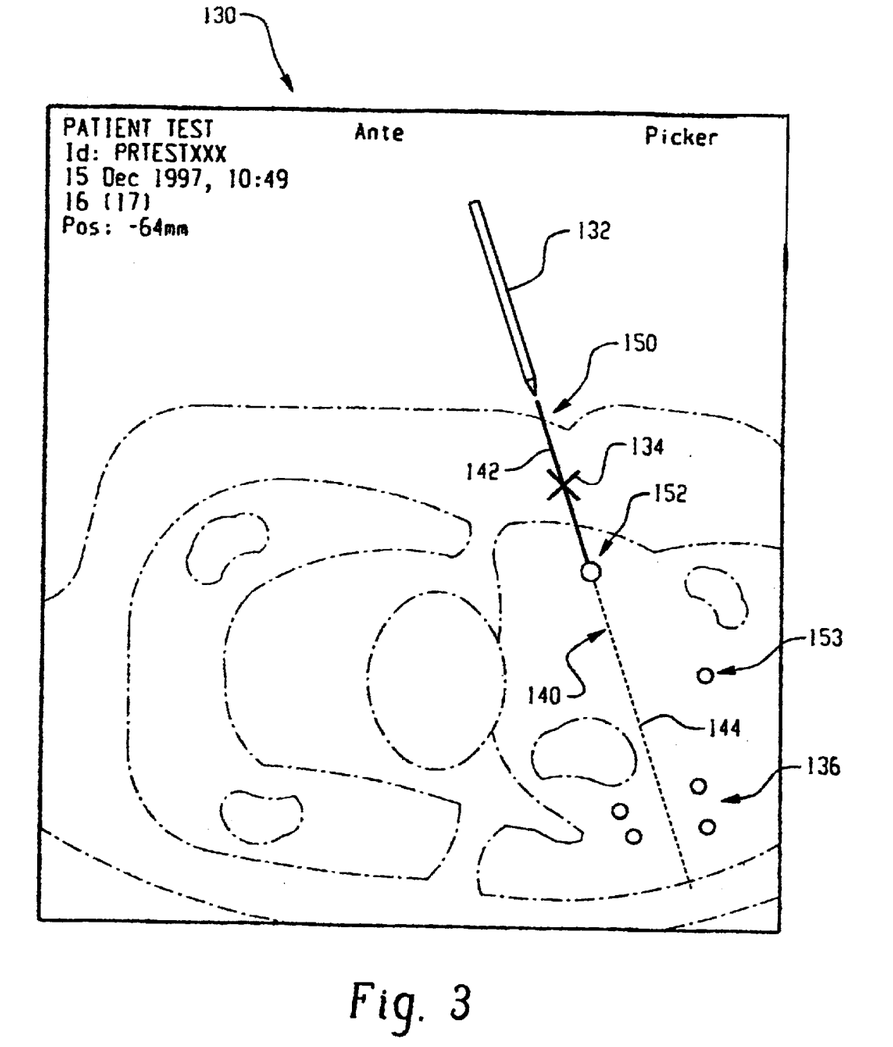
FIG. 3 is a view of an image slice formed from a patient and graphical symbols that are selectively placed on the image slice display according to the invention; and, FIGS. 4a–4c are illustrations showing a virtual bulls-eye displayed in various sizes and styles on a monitor to enable visualization of the correctness of the position and motion of a localizer device relative to a desired virtual planning trajectory and a virtual planning target point.

With reference to FIG. 3, in accordance with the present invention, during the planning stage before implementation of an interventional surgical procedure, a patient planning image 130 is presented on the planning image display 126. The at least one patient planning image 130 is preferably a single image slice drawn from a first image volume data set generated by scanning the patient in the imaging device. Preferably, in accordance with the invention, at least five (5) image slices are contained in each image volume data set generated in a single patient scan.

Movement of a virtual surgical instrument 132 within the patient planning image 130 is preferably controlled at the interventionist's control console 38. However, the localizer device 50 can also selectively be used as well. In addition, movement of a set of virtual cross-hairs 134 is also preferably controlled at the interventionist's control console 38. However, the localizer device 50 can also selectively be used as well. Preferably, the control console includes at least one operator interface device 39 (FIG. 2) to enable the operator to point to a plurality of selected virtual locations on one or more sectional planning images 130 of the patient shown on the planning image display 126. In the embodiment illustrated, the interface device 39 is a standard mouse, but other "pointing" type devices can be used as well including a trackball, a joystick or the like.

In accordance with a first preferred embodiment of the present invention, the form of presentation of the patient planning image 130 to be shown on the planning image display 126 is planned by placing a plurality of graphical point symbols 136 in the first sectional image 130 of the patient using the virtual cross-hairs 134 and the interface device 39 or, alternatively, using the localizer device 50. The plurality of graphical point symbols 136 selectively placed in the first sectional image 130 define a boundary in the image volume data set to be displayed in a subsequent sectional image of the patient to be displayed.

In a first form, the second sectional image of the patient to be displayed is derived by the present invention using exclusively the set of image slices contained in the data stored in the volumetric planning data memory 122 without further processing. The data is merely scaled or otherwise manipulated (but without interpolation) so that the boundary in the image volume data set is displayed to fill the planning image display 126.

In a second form, the second sectional image of the patient to be displayed is derived using the set of image slices contained in the data stored in the volumetric planning data memory 122 after additional further processing. The data comprising the first image volume data set is preferably interpolated and then scaled so that the boundary in the interpolated image volume data set is displayed to fill the planning image display 126.

In a third form, the second sectional image of the patient to be displayed is derived by re-scanning the patient in the imaging device 10 to acquire a second image volume data set and to generate a new set of image slices for storage in the volumetric planning data memory 122. Preferably, the second area of the patient to be re-scanned is defined by and bounded by the plurality of graphical point symbols 136 that were selectively placed in the first sectional image 130. The collected data from the patient re-scan is scaled so that the boundary in the new image volume data set is displayed to fill the planning image display 126.

Each of the above forms of deriving the second image volume data set is selectively available to an interventionist using suitable controls at the operator control console 38. The first form provides the quickest update in the displayed image. The second form provides a somewhat slower image display update, but presents a more comprehensive overall view of the virtual anatomy. As indicated above, however, interpolation typically degrades the image quality and affects image appearance. The third form provides the slowest image update but presents the most detailed view of the portion of the patient's anatomy selected from the first image slice.

With continued reference to FIG. 3, a virtual surgical instrument 132 is shown superimposed on the patient planning image 130. The position and orientation of the virtual surgical instrument 132 is selected and controlled at the operator console 38 using the interface device 39 or, alternatively, by using a physical localizer 50. The virtual surgical instrument 132 defines a virtual tool trajectory 140 extending through the patient planning image 130. It is an advantage of the present invention that the virtual tool trajectory 140 is represented in a first graphical form 142 for a first portion thereof extending on a first side of the image slice shown on the display as the patient planning image 130. Also, it is a further advantage of the present invention that the virtual tool trajectory 140 is represented in a second graphical form 144 for a second portion thereof extending on a second side of the image slice shown on the display as the patient planning image 130.

The presentation of the virtual tool trajectory 140 in two distinct graphical forms enables easy, quick and accurate visualization of the trajectory in a 3-D conceptual form even though the patient planning image is in reality essentially a two-dimensional image. In that way, an interventionist can recognize first portions 142 of the virtual tool trajectory 140 that lie "between" the interventionist and the plane of the image slice defining the patient planning image. In addition, the interventionist can recognize second portions 144 of the virtual tool trajectory 140 that lie "beyond" the plane of the image slice defining the patient planning image. In addition, each of the plurality of graphical symbols 136 including a virtual entry point 150, a virtual target point 152, a pivot point 153, cross-hairs 134, etc. are similarly represented to enable a "3-dimensional" planning visualization in a 2-dimensional image 130.

With continued reference to FIG. 3, the interventionist can, as an alternative to the above, define the virtual tool trajectory 140 by selecting a virtual entry point 150 and a virtual target point 152 on the image of the patient by placing the virtual cross-hairs 134 at a selected positions on the patient planning image 130 and actuating one or more suitable control switches (not shown). Target and entry points that lie "between" the interventionist and the plane of the image slice defining the patient planning image are displayed in a first unique graphical form such as, for example, as differently colored highlighted points. Similarly, target and entry points that lie "beyond" the plane of the image slice defining the patient planning image are displayed in a second unique graphical form such as, for example, as differently colored flashing or strobed points.

Figure 4A:
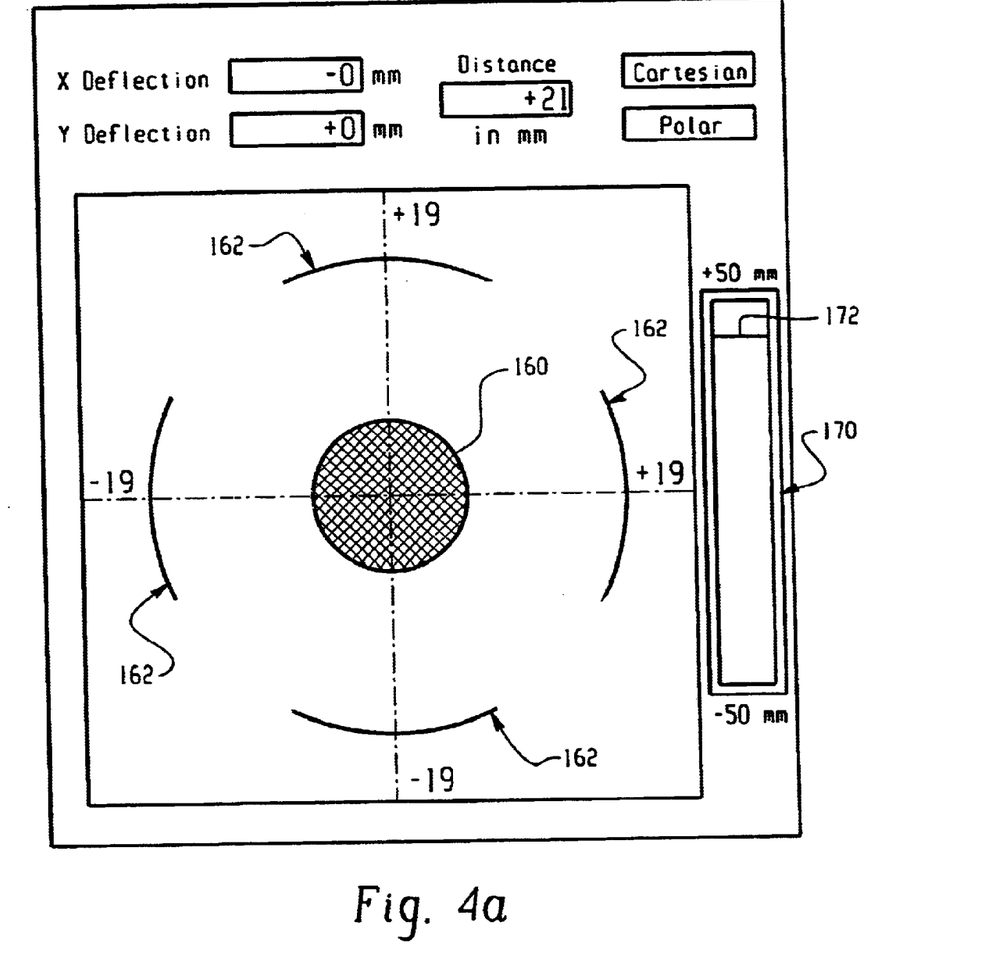

After the virtual target point 152 is selected in accordance with the above, the present invention provides means for interactive guidance of physical surgical tools into the body of the patient along the planning trajectory as represented by the virtual tool trajectory 140. Preferably, with reference now to FIGS. 4a–4c, a virtual bulls-eye 160 and a virtual proximity scale 170 are displayed on the operator console 38 to assist interventionists while introducing surgical tools into the patient.

The virtual bulls-eye 160 and scale 170 are responsive to the position and orientation of the localizer device 50 as tracked by the optical tracking system to provide a visual real time indication of the correctness of the tool path defined by the position of the localizer. More particularly, the size of the virtual bulls-eye 160 displayed becomes slightly larger, from the size shown in FIG. 4a to the size shown in FIG. 4b, when the physical localizer device 50 is aligned with the virtual tool trajectory 140. Also, the position of the proximity scale 170 changes from the indicator position 172 to the indicator position 174.

Figure 4B:
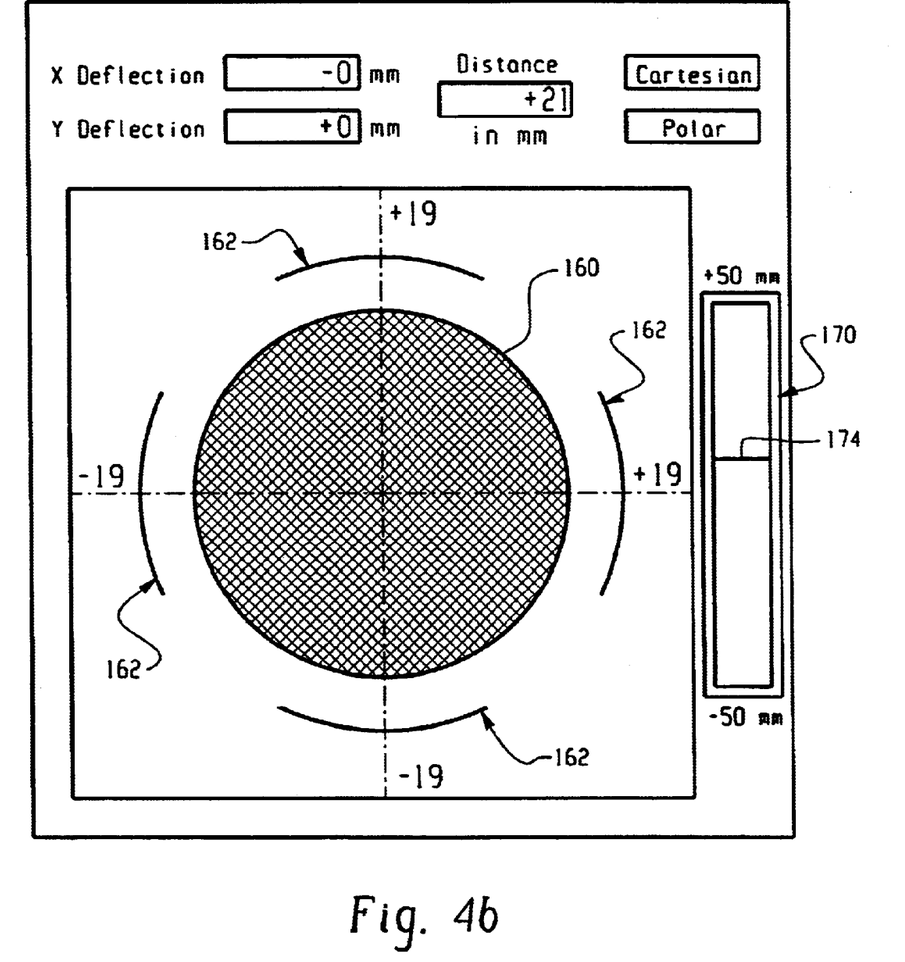
Figure 4C:
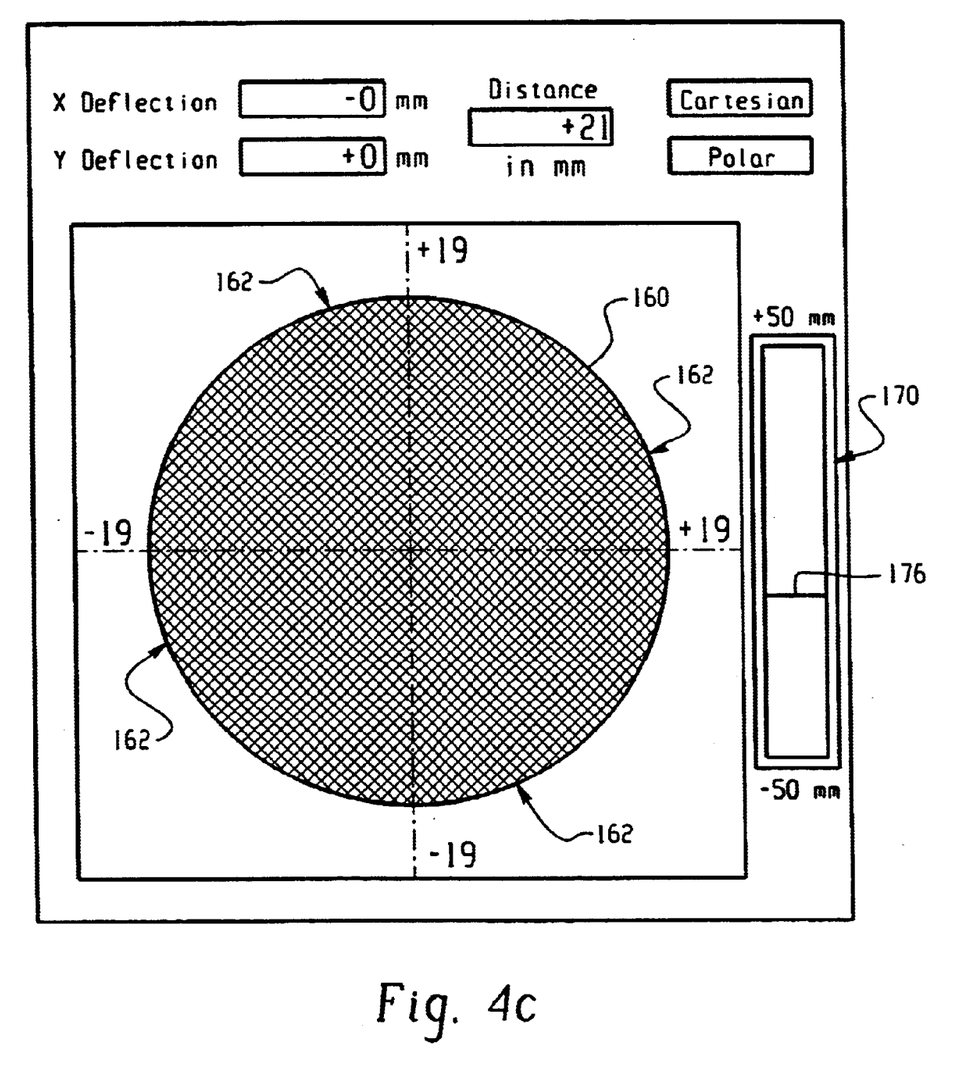

In addition, the size of the virtual bulls-eye 160 grows slightly from the size shown in FIG. 4b to the size shown in FIG. 4c when the physical localizer device 50 is advanced along a path defined in a virtual planning space by the virtual tool trajectory 140 towards the target point within the patient. Further, the position of the proximity scale 170 changes from the position 174 to the indicator position 176. Preferably, the virtual bulls-eye 160 is increased in size to completely fill the outer scope scale 162 when the surgical tool 52 reaches the target point. In that way, the interventionist is provided with a real time visualization of the progress of the introduction of the surgical tool into the patient's body.

Further, the color of the virtual bulls-eye 160 changes such as, for example, from red to blue, when the surgical tool is advanced beyond the selected target point. In addition, preferably, the size of the vertical bulls-eye 160 is decreased and the portion shown on the virtual scale 170 is changed in proportion to the distance that the surgical tool is moved beyond the selected target point. The interventionist is thereby provided with further real time visualization of the progress of the correctness of the introduction of the surgical tool into the patient's body.

The invention has been described with reference to the preferred embodiments. Obviously, modifications and alterations will occur to others upon reading and understanding the preceding description. It is intended that the invention be construed as including all such modifications and alterations insofar as they come within the scope of the appended claims or the equivalents thereof.

Having thus described the invention, it is claimed:

1. A method of planning a surgical procedure for inserting an object into a patient along a surgical planning trajectory from an entry point on the patient to a target point within the patient, the method comprising the steps of:

using an imaging device, performing a first scan of the patient to generate a first image volume data set of a first area of the patient;

using a human readable display device associated with, the imaging device, displaying a first sectional image of the patient based on said first image volume data set;

using an operator interface device associated with the imaging device, planning the surgical procedure on the patient by placing a plurality of graphical point symbols in said first sectional image of the patient displayed on the display device, the plurality of graphical point symbols defining a boundary of a second area of the patient for display on said human readable display device; and, displaying a second sectional image of the patient on said display device, the second sectional image being contained substantially entirely within the second area of the patient.

2. The method according to claim 1 further including the step of:

deriving said second sectional image of the patient directly from said first image volume data set.

3. The method according to claim 2 wherein the step of deriving said second sectional image includes deriving said second sectional image by computing a reformatted sectional image based on an interpolation of said first image volume data set.

4. The method according to claim 1 further including the steps of:

using said imaging device, performing a second scan of the patient to generate a second image volume data set of the patient, the second image volume data set being derived from said second area of the patient defined by said boundary; and, displaying said second sectional image of the patient based on said second image volume data set.

5. A method of planning a surgical procedure for inserting an object into a patient along a surgical planning trajectory from an entry point on the patient to a target point within the patient, the method comprising the steps of:

using an imaging device, performing a first scan of the patient to generate a first image volume data set of a first area of the patient;

using a human readable display device associated with the imaging device, displaying a first sectional image of the patient based on said first image volume data set; and, using an operator interface device associated with the imaging device, planning the surgical procedure on the patient by:

placing a plurality of graphical point symbols in said first sectional image of the patient displayed on the display device, the plurality of graphical point symbols defining a virtual trajectory extending in said first area of the patient; and, displaying indicia of a position of each of the plurality of graphical point symbols relative to a plane through said first image volume data set defining said first sectional image, the indicia including: first indicia indicating first ones of said graphical point symbols being located between a plane of said first sectional image displayed on said display device and a human observer of the display device; second indicia indicating second ones of said graphical point symbols being located behind said plane displayed on said display device relative to said human observer of the display device; and, third indicia indicating a relative distance between said graphical point symbols and said plane.

6. The method according to claim 5 wherein the step of planning said surgical procedure on the patient by placing said plurality of graphical point symbols in said first sectional image includes:

placing a first graphical point symbol in said first sectional image representative of a target point for an interventional surgical procedure on said patient; and, placing a second graphical point symbol in said first sectional image representative of an entry point for the interventional procedure on said patient.

7. The method according to claim 6 wherein the step of planning said surgical procedure the patient includes:

planning a second scan of the patient to generate a second sectional image of the patient orthogonal to a line connecting said entry point to said target point.

8. The method according to claim 7 wherein the step of planning said second scan of the patient includes planning said second scan of the patient to generate said second sectional image of the patient in a plane passing through a third selected point and orthogonal to said line connecting said entry point to said target point.

9. The method according to claim 7 further including the step of displaying, on said human readable display device, at least a portion of said line connecting said entry point to said target point.

10. The method according to claim 9 wherein the step of displaying said at least a portion of said line connecting said entry point to said target point includes displaying an orthogonal projection of said line on said second sectional image of the patient.

11. The method according to claim 6 wherein the step of planning said second scan of the patient to generate said second image volume data set of said patient includes:

planning said second scan of the patient to generate a second sectional image of the patient parallel to a line connecting said entry point to said target point.

12. The method according to claim 11 further including the step of displaying, on said human readable display device together with said first sectional image of said patient:

an angle of inclination of said line connecting said entry point to said target point relative to a first datum; and, an angle of declination of said line connecting said entry point to said target point relative to said first datum.

13. The method according to claim 12 wherein the displaying steps include displaying said first indicia, said second indicia, said third indicia, said target point, said entry point, said distance along said line, said angle of inclination, and said angle of declination in a form suitable for direct use by associated surgical equipment to enable an operator of said associated surgical equipment to define at least a point and an angle of entry of an associated interventional tool into the patient.

14. The method according to claim 6 further including the step of displaying, on said human readable display device, a line connecting said entry point to said target point and distance indicia representative of a length of said line connecting said entry point to said target point.

15. The method according to claim 14 further including the step of displaying intersection indicia, on said human readable display device, of a point of intersection between said first sectional image of said patient and said line connecting said entry point to said target point.

16. The method according to claim 15 further including the step of displaying at least one of said plurality of graphical point symbols as a pivot point in said first image volume data set, the pivot point together with said entry point and said target point defining a plane through said first image volume data set.

17. The method according to claim 5 further including the step of displaying, on said human readable display device, relative coordinates of each of said plurality of graphical point symbols.

18. An interface system for use with an associated imaging device selectively operative to perform a scan of a patient to generate a first image volume data set of the patient, the interface system comprising:

a human readable display device associated with the imaging device for selectively displaying a plurality of first image slices of said patient taken from said first image volume data set; and, an operator interface device associated with the imaging device and operative to define spatial properties of a second set of image slices to be taken from said first image volume data set by:

selectively placing a plurality of graphical point symbols in said plurality of first image slices of the patient displayed on the display device to define a boundary in the first image volume date set; and, displaying said second set of image slices on said display device, the second set of image slices being contained entirely within said boundary.

19. The interface system according to claim 18 further including interpolating means for generating said second set of image slices by interpolating said first image volume data set.

20. The interface system according to claim 19 further including means for generating said second set of image slices as a maximum intensity projection image of said first image volume data set, the maximum intensity projection image representing a three-dimensional rendering of selected tissue within said patient.

21. An interface system for use in an imaging device adapted to generate a first image volume data set of a patient and form image slices of the first image volume data set for display on a human-readable display monitor, the interface system comprising:

a display processor for generating a first set of image slices for display on the human-readable display monitor, the display processor delivering at least one image slice of the first set of image slices to the human-readable display monitor for display as a first sectional image;

a localizer device selectively movable into a plurality of positions relative to the patient and the imaging device, the localizer device being adapted to selectively carry an associated surgical tool thereon;

a position processor for determining a position of the localizer device relative to the patient and the imaging device, the position processor generating a localizer device position signal wherein the display processor is adapted to display a virtual image of the localizer device on said human-readable display monitor overlayed in relative registration on said first sectional image based on said localizer device position signal; and, means for displaying first indicia in association with said virtual image of the localizer device, the first indicia being representative of virtual position of the localizer device relative to a plane defined by said first sectional image, the indicia including first indicia indicating said virtual image being located between said plane on the display device and a human observer of the display device and second indicia indicating the virtual image being located behind said plane of the display device relative to said human observer of the display device.

22. The interface system according to claim 21 wherein the display processor is adapted to display a virtual image of a interventional needle on said human-readable display monitor, the interventional needle defining a virtual trajectory in said first sectional image.

23. The interface system according to claim 22 wherein the display processor is adapted to display at least a portion of the virtual trajectory in a form to enable visualization of a correctness of a path of the virtual trajectory relative to a preselected virtual target point in said first sectional image.

24. The interface systems according to claim 23 further including an operator interface device for selective placement of a plurality of graphical point symbols in said first sectional image displayed on said human-readable display monitor.

25. The interface system according to claim 24 further including means for generating at least one of an audible cue and a visual cue representative of said virtual trajectory being in substantial alignment with at least one of said plurality of graphical point symbols.

26. The interface system according to claim 25 wherein:
at least one of said graphical point symbols is a selected entry point of the virtual trajectory into the body of the patient; and,
said generating means is adapted to generate said at least one of said audible cue and said visual cue when the surgical instrument carried on the localizing device touches said entry point on said patient.

27. The interface system according to claim 25 wherein:
at least one of said graphical point symbols is a selected target point of the virtual trajectory within the body of the patient; and,
said generating means is adapted to generate said at least one of said audible cue and said visual cue in proportion to a relative distance between the surgical instrument carried on the localizing device and said target point within said patient.

28. The interface system according to claim 27 wherein he generating means is adapted to generated said at least one of said audible cue and visual cue in a spatial form representative of said correctness of said path of said virtual trajectory relative to a preselected virtual target point.

29. The interface system according to claim 23 wherein the display processor includes means for displaying indicia representative of a proximate relationship between said virtual trajectory and said target point.

30. The interface system according to claim 29 wherein said indicia is formed on the human-readable display monitor in the shape of a gun target.

31. The interface system according to claim 30 wherein said indicia formed in the shape of said gun target changes in appearance as the localizer device approaches the target point.

32. The interface system according to claim 31 wherein said indicia formed in the shape of said gun target changes in appearance when the surgical instrument reaches the target point.

* * * * *